United States Patent
Stasch et al.

(10) Patent No.: US 7,291,622 B2
(45) Date of Patent: *Nov. 6, 2007

(54) MEDICAL USES OF CARBAMATE-SUBSTITUTED PYRAZOLO-PYRIDINE DERIVATIVES

(75) Inventors: Johannes-Peter Stasch, Solingen (DE); Achim Feurer, Wilhelmsfeld (DE); Stefan Weigand, Wuppertal (DE); Elke Stahl, Bergisch Gladbach (DE); Dietmar Flubacher, Freiburg (DE); Cristina Alonso-Alija, Haan (DE); Frank Wunder, Wuppertal (DE); Dieter Lang, Velbert (DE); Klaus Dembowsky, Boston, MA (US); Alexander Straub, Wuppertal (DE); Elizabeth Perzborn, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/192,961

(22) Filed: Jul. 29, 2005

(65) Prior Publication Data

US 2005/0261323 A1 Nov. 24, 2005

Related U.S. Application Data

(63) Continuation of application No. 10/432,571, filed as application No. PCT/EP01/12966 on Nov. 9, 2001, now Pat. No. 7,105,523.

(30) Foreign Application Priority Data

Nov. 22, 2000 (DE) ................. 100 57 751

(51) Int. Cl.
A61K 31/437 (2006.01)
C07D 403/04 (2006.01)

(52) U.S. Cl. .................. 514/256; 544/298; 544/327; 544/328

(58) Field of Classification Search ............... 544/298, 544/327, 328; 514/256, 269
See application file for complete search history.

(56) References Cited

U.S. PATENT DOCUMENTS

| | | | |
|---|---|---|---|
| 6,166,027 A | 12/2000 | Straub et al. | 514/269 |
| 6,180,656 B1 | 1/2001 | Furstner et al. | 514/406 |
| 6,387,940 B1 | 5/2002 | Straub et al. | 514/403 |
| 6,410,740 B1 | 6/2002 | Straub et al. | 548/235 |
| 6,414,009 B1 | 7/2002 | Straub et al. | 514/403 |
| 6,451,805 B1 | 9/2002 | Straub et al. | 514/269 |
| 6,462,068 B1 | 10/2002 | Straub et al. | 514/403 |
| 7,105,523 B2 * | 9/2006 | Stasch et al. | 514/256 |

FOREIGN PATENT DOCUMENTS

| | | |
|---|---|---|
| WO | 9816223 | 4/1998 |
| WO | 9816507 | 4/1998 |
| WO | 9823619 | 5/1998 |
| WO | 0006567 | 2/2000 |
| WO | 0006568 | 2/2000 |
| WO | 0006569 | 2/2000 |
| WO | 0021954 | 4/2000 |

OTHER PUBLICATIONS

Vemulapalli et al., Medline Abstract (Life Sciences, vol. 67, Issue 1, pp. 23-29) May 2000.*
Weidmann, PubMed Abstract (Ther Umsch 55(6):384-8) Jun. 1998.*
Ko et al., "YC-1, a Novel Activator of Platelet Guanylate Cyclase", Blood 84 4226-4233 (1994).
Mulsch, et al., "Effect of YC-1, and NO-independent, Superoxide-Sensitive stimulator of Soluble Guanylyl Cyclase, on Smooth Muscle Responsiveness to Nitrovasodilators", Brit. J. of Pharmacol. 120 681-689 (1997).
Glass et al., "Stimulation of Human Platelet Guanylate Cyclase by Fatty Acids", J. of Biol. Chem. 252 1279-1285 (1977).
Pettibone et al., "A Structurally Novel Stimulator of Guanylate Cyclase with Long-lasting Hypotensive Activity in the Dog". Euro. J. of Pharmacol. 116, 307-312 (1985).
Yu et al., "Vasorelaxant Effect of Isoliquiritigenin, a Novel Soluble Gyanylate Cyclase Activator, in Rat Aorta" Brit. J. of Pharmacol. 114 1587-1594 (1995).
Damasio, Alzheimer's Disease and Related Dementias, Cecil Textbook of Medicine, 20th Edition, vol. 2, pp. 1992-1996, 1996.
Layzer, Robert B., Degenerative Diseases of the Nervous system, Cecil Textbook of Medicine, 20th Edition, vol. 2, pp. 2050-2057, 1996.
Wolin, et al. Review: Oxidant-NO Signalling Mechanism in Vascular Tissue, Biochemistry (Moscow), vol. 63, No. 7, 810/958, 1998.
Prandoni, The treatment of venous thromboembolic disorders: new challenges and opportunities, Haematologica/Journal of Haematology, vol. 88(05), pp. 610-613, 2003.
Fisker et al., PubMed Abstract (J. Endocrin Invest. 22 (5 Supply): 89-93), 1999.

* cited by examiner

*Primary Examiner*—Deepak Rao

(57) ABSTRACT

This invention relates to methods for treating sexual dysfunction, by administering a compound of the formula

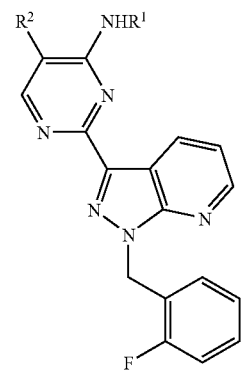

wherein $R^1$ is H or a di-$C_{1-6}$-alkylaminocarbonyl radical, and $R^2$ is a radical of the formula —O—C(X)—$NR^3R^4$ wherein X is O or S. The compound may also be administered in combination with at least one organic nitrate or NO donor, or in combination with at least one compound which inhibits the breakdown of cyclic guanosine monophosphate (cGMP).

3 Claims, No Drawings

MEDICAL USES OF CARBAMATE-SUBSTITUTED PYRAZOLO-PYRIDINE DERIVATIVES

This application is a continuation of application Ser. No. 10/432,571 filed Oct. 23, 2003 now U.S. Pat. No. 7,105,523 which is a 371 of PCT/EP01/12966 filed Nov. 9, 2001.

The present invention relates to novel chemical compounds which stimulate soluble guanylate cyclase, to the preparation thereof and to the use thereof as medicaments, in particular as medicaments for the treatment of cardiovascular disorders.

One of the most important cellular transmission systems in mammalian cells is cyclic guanosine monoposphate (cGMP). Together with nitric oxide (NO), which is released from the endothelium and transmits hormonal and mechanical signals, it forms the NO/cGMP system. Guanylate cyclases catalyse the biosynthesis of cGMP from guanosine triposphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. CO is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signal pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole (YC-1, Wu et al., Blood 84 (1994), 4226; Mülsch et al., Brit. J. Pharmacol. 120 (1997), 681; fatty acids (Goldberg et al, J. Biol. Chem. 252 (1977), 1279), diphenyliodonium hexafluorophosphate (Pettibone et al., Eur. J. Pharmacol. 116 (1985), 307), isoliquiritigenin (Yu et al., Brit. J. Pharmacol. 114 (1995), 1587) and various substituted pyrazole derivatives (WO 98/16223).

In addition, WO 98/16507, WO 98/23619, WO 00/06567, WO 00/06568, WO 00/06569 and WO 00/21954 describe pyrazolopyridine derivatives as stimulators of soluble guanylate cyclase. Also described inter alia in these patent applications are pyrazolopyridines having a pyrimidine residue in position 3. Compounds of this type have very high in vitro activity in relation to stimulating soluble guanylate cyclase. However, it has emerged that these compounds have some disadvantages in respect of their in vivo properties such as, for example, their behavior in the liver, their pharmacokinetic behavior, their dose-response relation or their metabolic pathway.

It was therefore the object of the present invention to provide further pyrazolopyridine derivatives which act as stimulators of soluble guanylate cyclase but do not have the disadvantages, detailed above, of the compounds from the prior art.

This object is achieved according to the present invention by the compounds claimed in claim 1. This new class of pyrazolopyridine derivatives is distinguished by having in position 3 a pyrimidine residue which has a particular substitution pattern, namely a carbamate or thiocarbamate residue in position 5 of the pyrimidine ring, and an amino group or a dialkylamide group in position 4 of the pyrimidine ring.

The present invention specifically relates to compounds of the formula (I)

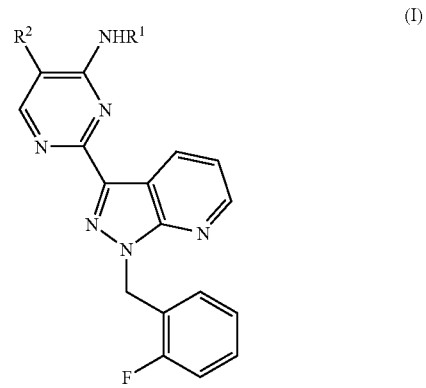

in which $R^1$ is hydrogen or a di-$C_{1-6}$-alkylaminocarbonyl radical, $R^2$ is a radical of the formula —O—CX—$NR^3R^4$, where X is O or S;

$R^3$ and $R^4$ may be identical or different from one another and is a radical from the group consisting of H, optionally substituted $C_{1-6}$-alkyl, optionally substituted $C_{1-6}$-alkoxy-$C_{1-6}$-alkyl, optionally substituted hydroxy-$C_{1-6}$-alkyl, optionally substituted $C_{2-6}$-alkenyl, optionally substituted $C_{1-6}$-alkylcarbonyloxy-$C_{1-6}$-alkyl, optionally substituted hydroxycarbonyl-$C_{1-6}$-alkyl, phenyl which is optionally substituted by a $C_{1-6}$-alkyl radical, or a saturated five- to seven-membered heterocycle which is optionally linked via a $C_{1-6}$-alkyl radical to the nitrogen atom, or optionally substituted $C_{3-8}$-cycloalkyl, where $R^3$ and $R^4$ cannot simultaneously be H;
or
$R^3$ and $R^4$ together with the nitrogen atom to which they are bonded form a five- to seven-membered saturated heterocycle which may optionally contain a further heteroatom from the group of N, O, S and/or may optionally be substituted or fused to a phenyl ring;

and salts, isomers and hydrates thereof.

Preference is given according to the present invention to compounds of the formula (I) in which
$R^1$ is hydrogen or a di-$C_{1-6}$-alkylaminocarbonyl radical,
$R^2$ is a radical of the formula —O—CX—NR$^3$R$^4$,
where
X is O or S;
$R^3$ and $R^4$ may be identical or different and is a radical from the group consisting of H, $C_{1-6}$-alkyl which optionally has a CN or a halogen substituent, $C_{1-6}$-alkoxy-$C_{1-6}$-alkyl, hydroxy-$C_{1-6}$-alkyl, $C_{2-6}$-alkenyl, $C_{1-6}$-alkylcarbonyloxy-$C_{1-6}$-alkyl, $C_{1-6}$-alkoxycarbonyl-$C_{1-6}$-alkyl, hydroxycarbonyl-$C_{1-6}$-alkyl, phenyl, p-tolyl, a saturated five- to seven-membered heterocycle which is linked via a $C_{1-6}$-alkanediyl radical to the nitrogen atom and has up to 2 oxygen atoms, or optionally substituted $C_{3-8}$-cycloalkyl, where $R^3$ and $R^4$ cannot simultaneously be H;
or
$R^3$ and $R^4$ together with the nitrogen atom to which they are bonded form a five- to seven-membered saturated heterocycle which may optionally contain a further heteroatom from the group of N, O, S and/or may optionally be substituted or fused to a phenyl ring;

and salts, isomers and hydrates thereof.

Particular preference is given in this connection to compounds of the formula (I) in which
$R^1$ is hydrogen or a diethylaminocarbonyl radical,
$R^2$ is a radical of the formula —O—CX—NR$^3$R$^4$,
where
X is O or S;
$R^3$ and $R^4$ may be identical or different and is a radical from the group consisting of H, methyl, ethyl, isopropyl, butan-2-yl, methoxyethyl, 2-methoxy-1-methylethyl, 1-cyano-1-methylethyl, 2-cyanoethyl, 2-chloroethyl, ethoxycarbonylmethyl, hydroxycarbonylmethyl, 2-propenyl, phenyl, p-tolyl, 1,3-dioxolan-2-methyl, cyclohexyl or cyclopentyl, where $R^3$ and $R^4$ cannot simultaneously be H;
or
$R^3$ and $R^4$ together with the nitrogen atom to which they are bonded form a five- or six-membered saturated heterocycle which may optionally contain a further heteroatom from the group of N, O and/or may optionally have a substituent from the group of methylcarbonyl, ethoxycarbonyl or t-butoxycarbonyl, or together are 1,2,3,4-tetrahydroquinolin-N-yl;

and salts, isomers and hydrates thereof.

The compounds of the invention of the general formula (I) may also be in the form of their salts. Mention may generally be made here of salts with organic or inorganic bases or acids.

Physiologically acceptable salts are preferred for the purposes of the present invention. Physiologically acceptable salts of the compounds according to the invention may be salts of the substances according to the invention with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, p-toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts may likewise be metal or ammonium salts of the compounds according to the invention having a free carboxyl group. Particularly preferred examples are sodium, potassium, magnesium or calcium salts, and ammonium salts derived from ammonia or organic amines such as, for example, ethylamine, di- or triethylamine, di- or triethanolamine, dicyclohexylamine, dimethylaminoethanol, arginine, lysine or ethylenediamine.

The compounds of the invention may exist in stereoisomeric forms which either are related as image and mirror image (enantiomers) or which are not related as image and mirror image (diastereomers). The invention relates both to the enantiomers or diastereomers and to respective mixtures thereof. The racemic forms can, just like the diastereomers, be separated into the stereoisomerically pure constituents in a known manner, for example by chromatographic separation. Double bonds present in the compounds of the invention may be in the cis or trans configuration (Z or E form).

A further possibility is for certain compounds to exist in tautomeric forms. This is known to the skilled person, and the invention likewise encompasses such compounds.

The compounds of the invention may also occur in the form of their hydrates, where the number of water molecules bound to the molecule depends on the particular compound of the invention.

Unless indicated otherwise, substituents generally have the following meaning for the purposes of the present invention:

Alkyl is generally a straight-chain or branched hydrocarbon radical having 1 to 20 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl, nonyl, decyl, dodeyl, eicosyl.

Alkylene is generally a straight-chain or branched hydrocarbon bridge having 1 to 20 carbon atoms. Examples which may be mentioned are methylene, ethylene, propylene, α-methylethylene, β-methylethylene, α-ethylethylene, β-ethylethylene, butylene, α-methylpropylene, β-methylpropylene, γ-methylpropylene, α-ethylpropylene, β-ethylpropylene, γ-ethylpropylene, pentylene, hexylene, heptylene, octylene, nonylene, decylene, dodeylene and eicosylene.

Alkenyl is generally a straight-chain or branched hydrocarbon radical having 2 to 20 carbon atoms and one or more, preferably having one or two, double bonds. Examples which may be mentioned are allyl, propenyl, isopropenyl, butenyl, isobutenyl, pentenyl, isopentenyl, hexenyl, isohexenyl, heptenyl, isoheptenyl, octenyl, isooctenyl.

Alkynyl is generally a straight-chain or branched hydrocarbon radical having 2 to 20 carbon atoms and one or more, preferably having one or two, triple bonds. Examples which may be named are ethynyl, 2-butynyl, 2-pentynyl and 2-hexynyl.

Acyl is generally straight-chain or branched lower alkyl having 1 to 9 carbon atoms which is linked via a carbonyl group. Examples which may be mentioned are: acetyl, ethylcarbonyl, propylcarbonyl, isopropylcarbonyl, butylcarbonyl and isobutylcarbonyl.

Alkoxy is generally a straight-chain or branched hydrocarbon radical having 1 to 14 carbon atoms which is linked via an oxygen atom. Examples which may be mentioned are methoxy, ethoxy, propoxy, isopropoxy, butoxy, isobutoxy, pentoxy isopentoxy, hexoxy, isohexoxy, heptoxy, isoheptoxy, octoxy or isooctoxy. The terms "alkoxy" and "alkyloxy" are used synonymously.

Alkoxyalkyl is generally an alkyl radical having up to 8 carbon atoms which is substituted by an alkoxy radical having up to 8 carbon atoms.

Alkoxycarbonyl may be represented for example by the formula

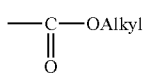

In this case, alkyl is generally a straight-chain or branched hydrocarbon radical having 1 to 13 carbon atoms. Examples which may be mentioned are the following alkoxycarbonyl radicals: methoxycarbonyl, ethoxycarbonyl, propoxycarbonyl, isopropoxycarbonyl, butoxycarbonyl or isobutoxycarbonyl.

Cycloalkyl is generally a cyclic hydrocarbon radical having 3 to 8 carbon atoms. Cyclopropyl, cyclopentyl and cyclohexyl are preferred. Examples which may be mentioned are cyclopentyl, cyclohexyl, cycloheptyl and cyclooctyl.

Cycloalkoxy is for the purposes of the invention an alkoxy radical whose hydrocarbon radical is a cycloalkyl radical. The cycloalkyl radical generally has up to 8 carbon atoms. Examples which may be mentioned are: cyclopyloxy and cyclohexyloxyl. The terms "cycloalkoxy" and "cycloalkyloxy" are used synonymously.

Aryl is generally an aromatic radical having 6 to 10 carbon atoms. Preferred aryl radicals are phenyl and naphthyl.

Halogen is for the purposes of the invention fluorine, chlorine, bromine and iodine.

Heterocycle is for the purposes of the invention in general a saturated, unsaturated or aromatic 3- to 10-membered, for example 5- or 6-membered, heterocycle which may contain up to 3 heteroatoms from the series S, N and/or O and, in the case of a nitrogen atom, also be bonded via the latter. Examples which may be mentioned are: oxadiazolyl, thiadiazolyl, pyrazolyl, pyridyl, pyrimidinyl, pyridazinyl, pyrazinyl, thienyl, furyl, pyrrolyl, pyrrolidinyl, piperazinyl, tetrahydropyranyl, tetrahydrofuranyl, 1,2,3 triazolyl, thiazolyl, oxazolyl, imidazolyl, morpholinyl or piperidyl. Preference is given to thiazolyl, furyl, oxazolyl, pyrazolyl, triazolyl, pyridyl, pyrimidinyl, pyridazinyl and tetrahydropyranyl. The term "heteroaryl" (or "hetaryl") stands for an aromatic heterocyclic radical.

The compounds of the invention of the formula (I) can be prepared by reacting the compound of the formula (II)

with the compound of the formula (III)

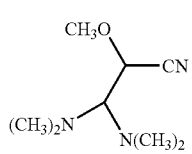

in an organic solvent in the presence of a base with heating and subsequently converting the ether group into the free hydroxyl group to give compounds of the formula (IV)

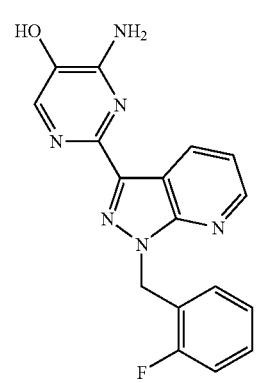

and subsequently reacting with compounds of the formula X—CO—NR³R⁴ in which

X is a halogen radical or alkoxy radical,

R³ and R⁴ have the meaning indicated above;

in an organic solvent, where appropriate in the presence of a base, and where appropriate with subsequent removal of protective groups to give compounds of the formula (I).

The compound of the formula (II) can be prepared as shown in the following reaction scheme:

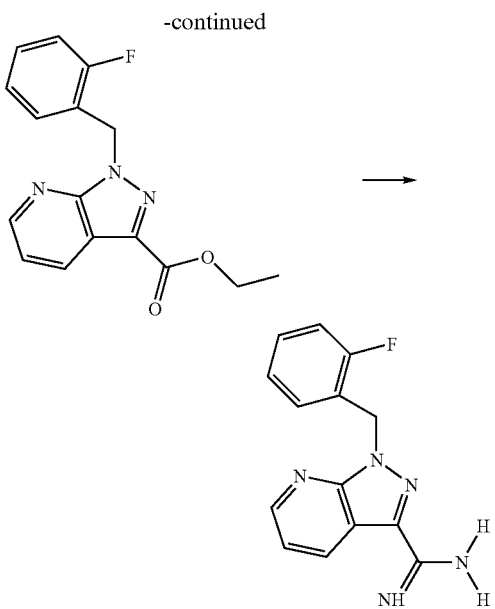

The compound of the formula (II) can be obtained in a multistage synthesis from the sodium salt of ethyl cyanopyruvate which is known from the literature (Borsche and Manteuffel, Liebigs. Ann. Chem. 1934, 512, 97). Reaction thereof with 2-fluorobenzylhydrazine with heating under a protective gas atmosphere in an inert solvent such as dioxane results in ethyl 5-amino-1-(2-fluorobenzyl)pyrazole-3-carboxylate, which cyclizes to the corresponding pyridine derivative by reaction with dimethylaminoacrolein or 1,1,3,3-tetramethoxypropane in acidic medium with heating under a protective gas atmosphere. This pyridine derivative ethyl 1-(2-fluorobenzyl)-1H-pyrazolo[3,4-b]pyridine-3-carboxylate is converted by a multistage sequence consisting of conversion of the ester with ammonia into the corresponding amide, dehydration with a dehydrating agent such as trifluoroacetic anhydride to the corresponding nitrile derivative, reaction of the nitrile derivative with sodium ethoxide and finally reaction with ammonium chloride into the compound of the formula (II).

The compound of the formula (III) can be prepared from the compounds, which can be purchased (e.g. from Aldrich), t-butoxybis(dimethylamino)methane and methoxyacetonitrile by reacting these reactants preferably in equimolar quantities, where appropriate in an organic inert solvent such as a cyclic ether, preferably dioxane, preferably under atmospheric pressure and stirring the reaction solution for several hours, for example 12 hours, at elevated temperature, for example 60-110° C., preferably 70-90° C., in particular 80° C.

Reaction of the compounds of the formulae (II) and (III) to give the compound of the formula (IV) can be carried out by employing the reactants in equimolar quantities or by using the compound of the formula (III) in slight excess in an organic solvent, for example an alcohol, preferably isoamyl alcohol in the presence of a small quantity of a base, for example an organic amine, in particular piperidine, preferably under atmospheric pressure and stirring the reaction solution for several hours, for example 12 hours, at elevated temperature, for example 60-130° C., preferably 80-120° C., in particular 110° C., and subsequently liberating the hydroxyl group by reacting the compound obtained in this way with a preferably equimolar quantity of a thiol such as, for example, thiophenol in the presence of a small quantity of a base such as an alkali metal base, for example an alkali metal carbonate, preferably potassium carbonate in an organic solvent such as, for example, 1-methyl-2-pyrrolidone, preferably under atmospheric pressure and stirring the reaction solution for some hours, for example 1 hour, at elevated temperature, for example 100-200° C., preferably 150-200° C.

The compounds of the formula (IV) can be reacted with compounds of the formula X—CONR³R⁴ where X, R³ and R⁴ are as defined above to give the compounds of the invention of the formula (I). These carbamoyl derivatives can either be purchased or be obtained in a manner known to the skilled worker. The reaction of appropriate secondary amines with phosgene or phosgene substitutes such as trichloromethyl chloroformate (diphosgene) or bis(trichloromethyl) carbonate (triphosgene) may be mentioned here by way of example (cf. J. March, Advanced Organic Synthesis, 3$^{rd}$ ed., Wiley 1985, 370, D. Hoppe, Synthesis 1996, 149-154). The secondary amines required for this can either be purchased or be obtained in a manner known to the skilled worker, for example by reacting a primary amine with an appropriate aldehyde or ketone using a reducing agent conventionally employed for such reactions, for example a metal hydride complex, preferably an alkali metal hydride complex such as sodium cyanoborohydride ("Reductive Amination", cf. K.-L. Yu, J. Ostrowski, P. Reczek, M. M. Mansuri, J. E. Starrett Jr., Synthetic Communications, 1995, 25, 2819-2827).

Reaction of the compounds of the formula (IV) with compounds of the formula X—CONR³R⁴ where X, R³ and R⁴ are as defined above to give the compounds of the invention of the formula (I) preferably takes place either in an organic solvent conventionally used for such reactions, such as, for example, a cyclic ether, in particular tetrahydrofuran (THF), in the presence of an equimolar quantity or of a slight excess of a base, with preference an alkali metal base, preferably of an alkali metal hydride and particularly preferably sodium hydride, preferably under atmospheric pressure and stirring the reaction solution for several hours, for example 12 hours, at room temperature. The reactants are in this case employed in equimolar quantities or the carbamoyl derivative in slight excess. Another possibility is to carry out the reaction in pyridine without another base, preferably under atmospheric pressure and stirring the reaction solution for some hours, for example 2 hours, at elevated temperature of 60 to 130° C., preferably 80 to 120° C. and in particular at 110° C.

Reaction of the compound of the formula (IV) with thiocarbamoyl chlorides to give the corresponding carbamates can also take place analogously. Reaction in pyridine is preferred. The thiocarbamoyl chlorides used according to the invention can be purchased.

It is subsequently possible for protective groups which are present where appropriate on the molecule to be removed in a manner known to the skilled worker. Concerning this, reference may be made for example to T. W. Greene, P. G. M. Wuts, Protective Groups in Organic Synthesis, second edition, New York, 1991, concerning possible protective groups and the removal thereof from the target compound.

The compounds of the invention of the general formula (I) show a valuable range of pharmacological effects which could not have been predicted.

The compounds of the invention of the general formula (I) lead to vasorelaxation, inhibition of platelet aggregation and to a reduction in blood pressure and to an increase in coronary blood flow. These effects are mediated by direct stimulation of soluble guanylate cyclase and an intracellular increase in cGMP. In addition, the compounds of the invention of the general formula (I) enhance the effect of substances which increase the cGMP level, such as, for example, EDRF (endothelium derived relaxing factor), NO donors, protoporphyrin IX, arachidonic acid or phenylhydrazine derivatives.

They can therefore be employed in medicaments for the treatment of cardiovascular disorders such as, for example, for the treatment of high blood pressure and heart failure, stable and unstable angina pectoris, peripheral and cardiac vascular disorders, of arrhythmias, for the treatment of thromboembolic disorders and ischemias such as myocardial infarction, stroke, transistorily and ischemic attacks, disturbances of peripheral blood flow, prevention of restenoses as after thrombolysis therapies, percutaneously transluminal angioplasties (PTAs), percutaneously transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, osteoporosis, gastroparesis and incontinence.

The compounds of the present invention of the general formula (I) are also active substances for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory loss, vascular dementia, craniocerebral trauma, stroke, dementia occurring after strokes (post stroke dementia), post-traumatic brain trauma, general concentration impairments, concentration impairments in children with learning and memory problems, Alzheimer's disease, vascular dementia, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The active ingredients are furthermore also suitable for controlling cerebral blood flow and thus represent effective agents for controlling migraines.

They are also suitable for the prophylaxis and control of the sequelae of cerebral infarctions such as stroke, cerebral ischemias and craniocerebral trauma. The compounds of the invention of the general formula (I) can likewise be employed for controlling states of pain.

In addition, the compounds of the invention have an anti-inflammatory effect and can therefore be employed as anti-inflammatory agents.

Furthermore, the present invention also encompasses the combination of the compounds of the invention of the general formula (I) with organic nitrates or NO donors.

Organic nitrates and NO donors for the purposes of the invention are generally substances which display their therapeutic effect via release of NO or NO species.

Sodium nitroprusside, nitroglycerin, isosorbide dinitrate, isosorbide mononitrate, molsidomine and SIN-1 are preferred.

In addition, the present invention also encompasses the combination with compounds which inhibit breakdown of cyclic guanosine monophosphate (cGMP). These are in particular inhibitors of phosphodiesterases 1, 2 and 5; nomenclature of Beavo and Reifsnyder (1990), TiPS 11 pp. 150 to 155. These inhibitors potentiate the effect of the compounds of the invention, and increase the desired pharmacological effect.

BIOLOGICAL INVESTIGATIONS

Vasorelaxant Effect In Vitro

Rabbits are stunned by a blow to the back of the neck and are exsanguinated. The aorta is removed, freed of adherent tissue and divided into rings 1.5 mm wide, which are put singly under tension in 5 ml organ baths containing carbogen-gassed Krebs-Henseleit solution at 37° C. with the following composition (mM): NaCl: 119; KCl: 4.8; $CaCl_2 \times 2H_2O$: 1; $MgSO_4 \times 7H_2O$: 1.4; $KH_2PO_4$: 1.2; $NaHCO_3$: 25; glucose: 10. The force of contraction is detected with Statham UC2 cells, amplified and digitized via A/D converters (DAS-1802 HC, Keithley Instruments Munich) and recorded in parallel on chart recorders. A contraction is generated by adding phenylephrine to the bath cumulatively in increasing concentration. After several control cycles, the substance to be investigated is investigated in each further run in increasing dosage in each case, and the height of the contraction is compared with the height of the contraction reached in the last preceding run. The concentration necessary to reduce the height of the control value by 50% ($IC_{50}$) is calculated from this. The standard application volume is 5 µl, and the DMSO content in the bath solution corresponds to 0.1%. The results are listed in Table 1 below:

TABLE 1

| Vasorelaxant effect in vitro | |
|---|---|
| Example no. | $IC_{50}$ [µM] |
| 2 | 0.65 |
| 6 | 0.27 |
| 11 | 0.52 |
| 15 | 0.32 |
| 19 | 0.42 |
| 26 | 0.34 |

Determination of the Liver Clearance In Vitro

Rats are anesthetized and heparinized, and the liver is perfused in situ via the portal vein. Primary rat hepatocytes are then obtained ex vivo from the liver using collagenase solution. $2 \cdot 10^6$ hepatocytes per ml were incubated with in each case the same concentration of the compound to be investigated at 37° C. The decrease in the substrate to be investigated over time was determined bioanalytically (HPLC/UV, HPLC/fluorescence or LC/MSMS) at 5 time points in each case in the period 0-15 min after the start of incubation. The clearance was calculated therefrom via the number of cells and the weight of the liver.

Determination of the Plasma Clearance In Vivo

The substance to be investigated is administered intravenously as solution to rats via the tail vein. Blood is taken from the rats at fixed times and is heparinized, and plasma is obtained therefrom by conventional procedures. The substance is quantified in the plasma bioanalytically. The pharmacokinetic parameters are calculated from the plasma concentration/time courses found in this way via conventional non-compartmental methods used for this purpose.

The present invention includes pharmaceutical preparations which, besides non-toxic, inert pharmaceutically suitable carriers, comprise the compounds of the invention of the general formula (I), and process for the production of these preparations.

The active ingredient may, where appropriate, also be present in microencapsulated form in one or more of the carriers indicated above.

The therapeutically effective compounds of the general formula (I) should be present in the pharmaceutical preparations mentioned above in a concentration of about 0.1 to 99.5, preferably of about 0.5 to 95, % by weight of the complete mixture.

The pharmaceutical preparations mentioned above may, apart from the compounds of the invention of the general formula (I), also comprise other active pharmaceutical ingredients.

It has generally proved advantageous both in human and in veterinary medicine to administer the active ingredient(s) of the invention in total amounts of about 0.01 to about 700, preferably 0.01 to 100, mg/kg of body weight per 24 hours, where appropriate in the form of a plurality of single doses, to achieve the desired results. A single dose preferably contains the active ingredients of the invention in amounts of about 0.1 to about 80, in particular 0.1 to 30, mg/kg of body weight.

The present invention is explained in more detail below by means of non-restrictive preferred examples. Unless indicated elsewhere, all quantitative data relate to percentages by weight.

EXAMPLES

Abbreviations:

| RT: | Room temperature |
| EA: | Ethyl acetate |
| MCPBA: | m-Chloroperoxybenzoic acid |
| BABA: | n-Butyl acetate/n-butanol/glacial acetic acid/phosphate buffer pH 6 (50:9:25.15; org. phase) |
| DMF: | N,N-Dimethylformamide |

Mobile Phases for Thin-Layer Chromatography:

| T1 E1: | Toluene/ethyl acetate (1:1) |
| T1 EtOH1: | Toluene/methanol (1:1) |
| C1 E1: | Cyclohexane/ethyl acetate (1:1) |
| C1 E2: | Cyclohexane/ethyl acetate (1:2) |

Methods for Determining the HPLC Retention Times:

Method A (HPLC-MS):
Eluent: A=$CH_3CN$ B=0.6 g 30% HCl/1$H_2O$
Flow rate: 0.6 ml/min
Column oven: 50° C.
Column: Symmetry C18 2.1*150 mm
Gradient:

| Time (min) | % A | % B | Flow rate (ml/min) |
|---|---|---|---|
| 0 | 10 | 90 | 0.6 |
| 4 | 90 | 10 | 0.6 |
| 9 | 90 | 10 | 0.8 |

Method B (HPLC):
Eluent: A=5 ml $HClO_4$/A $H_2O$, B=$CH_3CN$
Flow rate: 0.75 ml/min
L-R temperature: 30.00° C. 29.99° C.
Column: Kromasil C18 60*2 mm
Gradient:

| Time (min) | % A | % B |
|---|---|---|
| 0.50 | 98 | 2 |
| 4.50 | 10 | 90 |
| 6.50 | 10 | 90 |
| 6.70 | 98 | 2 |
| 7.50 | 98 | 2 |

Method C(HPLC):
Eluent: A=$H_3PO_4$ 0.01 mol/l, B=$CH_3CN$
Flow rate: 0.75 ml/min
L-R temperature: 30.01° C. 29.98° C.
Column: Kromasil C18 60*2 mm
Gradient:

| Time (min) | % A | % B |
|---|---|---|
| 0.00 | 90 | 10 |
| 0.50 | 90 | 10 |
| 4.50 | 10 | 90 |
| 8.00 | 10 | 90 |
| 8.50 | 90 | 10 |
| 10.00 | 90 | 10 |

Method D (chiral HPLC):
Eluent: 50% isohexane, 50% ethanol
Flow rate: 1.00 ml/min
Temperature: 40° C.
Column: 250*4.6 mm, packed with Chiralcel OD, 10 μm Method E (HPLC-MS):
Eluent: A=$CH_3CN$ B=0.3 g 30% HCl/1 $H_{2O}$
Flow rate: 0.9 ml/min
Column oven: 50° C.
Column: Symmetry C 18 2.1*150 mm
Gradient:

| Time (min) | % A | % B | Flow rate (ml/min) |
|---|---|---|---|
| 0 | 10 | 90 | 0.9 |
| 3 | 90 | 10 | 1.2 |
| 6 | 90 | 10 | 1.2 |

Method F:
Eluent: A=$CH_3CN$+0.1% HCOOH B=$H_2O$+0.1% HCOOH
Column oven: 40° C.
Column: Symmetry C18 2.1*150 mm
Gradient:

| Time (min) | % A | % B | Flow rate (ml/min) |
|---|---|---|---|
| 0 | 10 | 90 | 0.5 |
| 4 | 90 | 10 | 0.5 |

-continued

| Time (min) | % A | % B | Flow rate (ml/min) |
|---|---|---|---|
| 6 | 90 | 10 | 0.5 |
| 6.1 | 10 | 90 | 1.0 |
| 7.5 | 10 | 90 | 0.5 |

Starting Compounds:

I. Synthesis of 3,3-bis(dimethylamino)-2-methoxypropionitrile

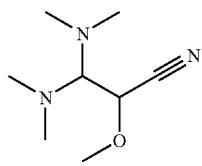

40.0 g (229.5 mmol) of ter-butoxybis(dimethylamino) methane and 16.3 g (229.5 mmol) of methoxyacetonitrile are stirred at 80° C. overnight. For workup, volatile material is stripped off in a rotary evaporator, and the residue is distilled in a kugelrohr under high vacuum at 140° C. The NMR spectrum (300 MHz, $D_6$-DMSO) shows that the product contains the enamine as E/Z mixture resulting from elimination of dimethylamine. The product mixture is employed in the next reaction without further purification.

Yield: 24.7 g (60%)

II. Synthesis of 1-(2-fluorobenzyl)1H-pyrazolo[3,4-b]pyridine-3-carboxamidine

2A) Ethyl 5-amino-1-(2-fluorobenzyl)pyrazol-3-carboxylate

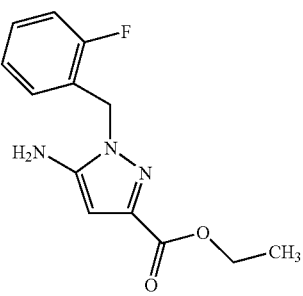

111.75 g (75 ml, 0.98 mol) of trifluoroacetic acid are added to 100 g (0.613 mmol) of the sodium salt of ethyl cyanopyruvate (preparation in analogy to Borsche and Manteuffel, Liebigs Ann. 1934, 512, 97) in 2.5 l of dioxane under argon at room temperature with efficient stirring, and the mixture is stirred for 10 min, during which most of the precursor dissolves. Then 85.93 g (0.613 mol) of 2-fluorobenzylhydrazine are added and the mixture is boiled overnight. After cooling, the sodium trifluoroacetate crystals which have separated out are filtered off with suction and washed with dioxane, and the crude solution is reacted further.

2B) Ethyl 1-(2-fluorobenzyl)-1H-pyrazolo[3,4-b]pyridine-3-carboxylate

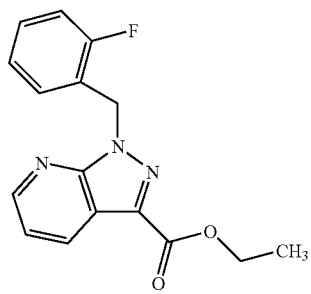

The solution obtained from 2A) is mixed with 61.25 ml (60.77 g, 0.613 mmol) of dimethylaminoacrolein and 56.28 ml (83.88 g, 0.736 mol) of trifluoroacetic acid and boiled under argon for 3 days. The solvent is then evaporated in vacuo, and the residue is added to 2 l of water and extracted three times with 1 l of ethyl acetate each time. The combined organic phases are dried over magnesium sulfate and concentrated in a rotary evaporator. Chromatography is carried out on 2.5 kg of silica gel, eluting with a toluene/toluene-ethyl acetate=4:1 gradient. Yield: 91.6 g (49.9% of theory over two stages).

Melting point 85° C. $R_f$ ($SiO_2$, T1E1): 0.83

2C) 1-(2-Fluorobenzyl)-1H-pyrazolo[3,4-b]pyridine-3-carboxamide

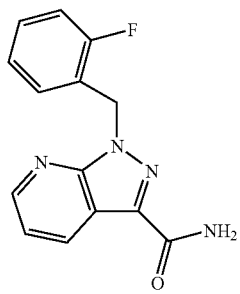

10.18 g (34 mmol) of the ester obtained in example 2B) are introduced into 150 ml of methanol saturated with ammonia at 0-10° C. Stirring at room temperature for two days is followed by concentration in vacuo.

$R_f$ ($SiO_2$, T1E1): 0.33

2D) 3-Cyano-1-(2-fluorobenzyl)-1H-pyrazolo[3,4-b]pyridine

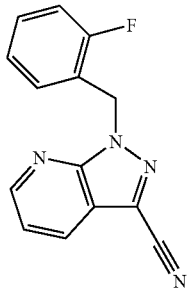

36.1 g (133 mmol) of 1-(2-fluorobenzyl)-1H-pyrazolo[3,4-b]pyridine-3-carboxamide from example 2C) are dissolved in 330 ml of THF, and 27 g (341 mmol) of pyridine are added. Then, over the course of 10 min, 47.76 ml (71.66 g, 341 mmol) of trifluoroacetic anhydride are added, during which the temperature rises to 40° C. The mixture is stirred at room temperature overnight. It is then added to 1l of water and extracted three times with 0.5l of ethyl acetate each time. The organic phase is washed with saturated sodium bicarbonate solution and with 1 N HCl, dried with MgSO4 and concentrated in a rotary evaporator.

Yield: 33.7 g (100% of theory) Melting point: 81° C. $R_f$ (SiO$_2$, T1E1): 0.74

2E) Methyl(2-fluorobenzyl)-1H-pyrazolo[3,4-b]pyridine-3-carboximidate

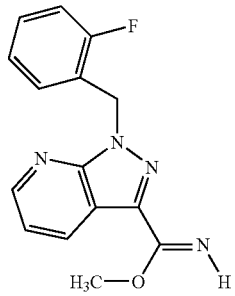

30.37 g (562 mmol) of sodium methoxide are dissolved in 1.5l of methanol, and 36.45 g (144.5 mmol) of 3-cyano-1-(2-fluorobenzyl)-1H-pyrazolo[3,4-b]pyridine (from example 2D) are added. The solution obtained after stirring at room temperature for 2 hours is employed directly for the next stage.

2F) 1-(2-Fluorobenzyl)-1H-pyrazolo[3,4-b]pyridine-3-carboxamidine

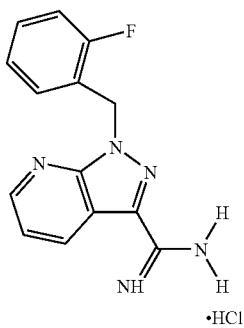

33.76 g (32.19 ml, 562 mmol) of glacial acetic acid and 9.28 g (173 mmol) of ammonium chloride are added to the solution of methyl(2-fluorobenzyl)-1H-pyrazolo[3,4-b]pyridine-3-carboximidate in methanol obtained from example 2E), and the mixture is stirred under reflux overnight. The solvent is evaporated in vacuo, the residue is thoroughly triturated with acetone, and the precipitated solid is filtered off with suction.

$^1$H-NMR (d$_6$-DMSO, 200 MHz): δ=5.93 (s, 2H); 7.1-7.5 (m, 4H); 7.55 (dd, 1H); 8.12 (dd, 1H); 8.30 (dd, 1H); 9.5 (bs, 4H-exchangeable) ppm.

ME (EI): m/z=270.2 (M−HCl)

III. Synthesis of 2-[1-(2-fluorobenzyl)-1H-pyrazolo[3,4-b]pyridin-3-yl]-5-methoxy-4-pyrimidinylamine

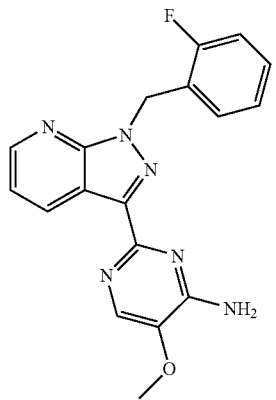

46.8 g (134.8 mmol) of 1-(2-fluorobenzyl)-1H-pyrazolo[3,4-b]pyridine-3-carboximidamide from example II are dissolved in isoamyl alcohol. To this are added 24.7 g (144.2 mmol) of 3,3-bis(dimethylamino)-2-methoxypropionitrile from example 1 and 1.15 g (1.33 ml, 13.5 mmol) of piperidine, and the mixture is left to stir at 110° C. for 3 days. For workup, it is cooled to 0° C., and the precipitated product is filtered off with suction, thoroughly washed with cold diethyl ether and dried in a vacuum oven at 50° C.

Yield: 25.4 g (52.7%) $R_f$: 0.34 (dichloromethane/methanol 20:1) $^1$H-NMR: (400 MHz, D$_6$-DMSO), δ=3.89 (2, 3H, OCH$_3$), 5.79 (s, 2H, CH$_2$), 6.93 (br. S, 2H, NH$_2$), 7.10-7.26 (m, 3H, Ar—H), 7.31-7.39 (m, 2H, Ar—H), 7.98 (s, 1H, pyrimidine-H), 8.61 (dd, 1H, pyridine-H), 8.92 (dd, 1H, pyridine-H) ME (EI): (ESI pos.), m/z=350.9 ([M+H]$^+$), 700.8 ([2M+H]$^+$)

IV. Synthesis of 4-amino-2-[1-(2-fluorobenzyl)-1H-pyrazolo[3,4-b]pyridin-3-yl]-5-pyrimidinol

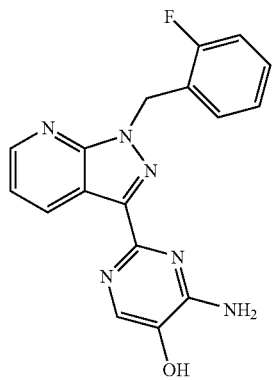

25.3 g (72.2 mmol) of 2-[1-(2-fluorobenzyl)-1H-pyrazolo[3,4-b]pyridin-3-yl]-5-methoxy-4-pyrimidinylamine from example III are dissolved in 500 ml of 1-methyl-2-pyrrolidone. To this are added 7.96 g (7.42 ml, 72.2 mmol) of thiophenol and 2.50 g (18.1 mmol) of potassium carbonate, and the mixture is left to stir at 190° C. for about 1 h. For workup, the solvent is condensed off, and the residue is mixed with half-conc. ammonium chloride solution and extracted three times with ethyl acetate. Most of the product precipitates during this. It is filtered off with suction and dried in a vacuum oven at 50° C.

Yield: 18.1 g (72.3%) $R_f$: 0.44 (dichloromethane/methanol 10:1) $^1$H-NMR: (300 MHz, $D_6$-DMSO), δ=5.78 (s, 2H, $CH_2$), 6.66 (br. S, 2H, $NH_2$), 7.09-7.38 (m, 5H, Ar—H), 7.82 (s, 1H, pyrimidine-H), 8.60 (dd, 1H, pyridine-H), 8.92 (dd, 1H, pyridine-H), 9.4-10.2 (br. S, 1H, OH) MS: (ESI pos.), m/z=337.3 ($[M+H]^+$), 673.3 ($[2M+H]^+$)

V. Synthesis of 3,4-dimethoxybenzyl(methyl)carbamoyl chloride

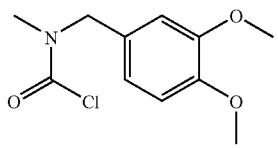

1.00 g (5.52 mmol) of 3,4-dimethoxybenzyl-N-methylamine (obtainable by reductive amination from 3,4-dimethoxybenzaldehyde) are dissolved in 20 ml of anhydrous pyridine. 0.60 g (0.37 mmol, 3.04 mmol) of trichloromethyl chloroformate ("diphosgene") is added, and the mixture is left to stir at room temperature overnight. The solution is employed without workup directly in the next stage.

VI. 4-Amino-2-[1-(2-fluorobenzyl)-1H-pyrazolo[3,4-b]pyridin-3-yl]-5-pyrimidinyl]3,4-dimethoxybenzyl(methyl)carbamate

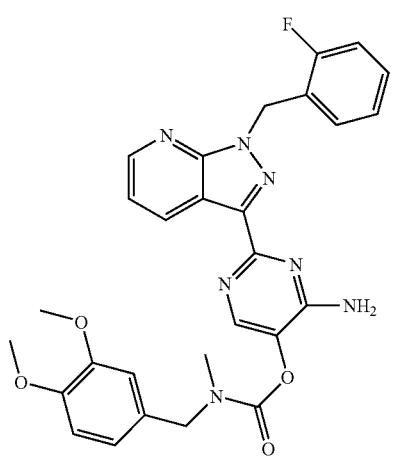

1.38 g (4.10 mmol) of 4-amino-2-[1-(2-fluorobenzyl)-1H-pyrazolo[3,4-b]pyridin-3-yl]-5-pyrimidinol from example IV are suspended in 100 ml of anhydrous pyridine and heated to 110° 0C. To this is added a solution of 1.20 g (4.92 mmol) of 3,4-dimethoxybenzyl(methyl)carbamoyl chloride from example V in 20 ml of anhydrous pyridine (from the reaction described above) and the mixture is left to stir at 110° C. for about 5 h. For workup, the reaction solution is concentrated in a rotary evaporator, and the residue is chromatographed on silica gel with dichloromethane/methanol (initially 100:1, then 50:1). The product contains, according to the NMR spectrum, an unknown impurity and is employed without further purification.

Rf: 0.90 (dichloromethane/methanol 10:1)

VII. Synthesis of allyl(cyclopentyl)carbamoyl chloride

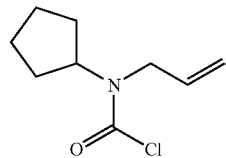

790 mg (0.48 ml, 3.99 mmol) of trichloromethylformate ("diphosgene") are dissolved in 15 ml of dichloromethane and cooled to 0° C. To this are slowly added dropwise 1.00 g (1.17 ml, 7.986 mmol) of allyl(cyclopentyl)amine and 1.21 g (1.67 ml, 12.0 mmol) of triethylamine, and the mixture is left to stir at room temperature overnight. For workup, the reaction solution is poured into ice-water, extracted three times with dichloromethane, dried over $MgSO_4$ and concentrated. The crude product is employed directly in the next stage.

MS: (E1), m/z (%)=187 (12, $[M]^+$, Cl), 152 (30, $[M-Cl]^+$), 120 (45), 69 (50), 41(100)

VIII. 4-Methoxybenzyl(2-methoxyethyl)carbamoyl chloride

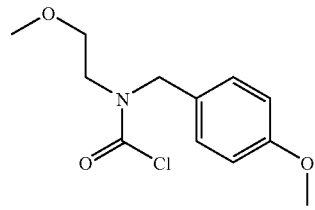

0.51 g (0.31 ml, 2.56 mmol) of trichloromethyl chloroformate ("diphosgene") are dissolved in 15 ml of dichloromethane, and 1.00 g (5.12 mmol) of 4-methoxybenzyl(2-methoxyethyl)amine and 0.78 g (7.68 mmol) of triethylamine are slowly added. After stirring at room temperature overnight, the mixture is poured into ice-water and extracted three times with dichloromethane, and the organic phase is dried over magnesium sulfate and concentrated to dryness in a rotary evaporator. The crude product is employed without workup directly in the next stage.

IX. 4-Amino-2-[1-(2-fluorobenzyl)-1H-pyrazolo[3,4-b]pyridin-3-yl]-5-pyrimidinyl 4-methoxybenzyl(2-methoxyethyl)carbamate

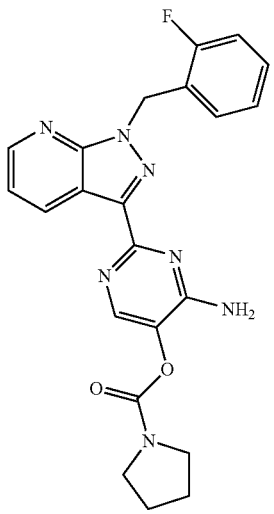

100 mg (0.30 mmol) of 4-amino-2-[1-(2-fluorobenzyl)-1H-pyrazolo[3,4-b]pyridin-3-yl]-5-pyrimidinol from example IV are suspended in 15 ml of anhydrous pyridine and heated to 110° C. To this are added 92.0 mg (0.36 mmol) of 4-methoxybenzyl(2-methoxyethyl)carbamoyl chloride from example VIII, and the mixture is left to stir at 110° C. for about 2 h. For workup, the reaction solution is concentrated in a rotary evaporator, the residue is taken up in dichloromethane and washed with saturated ammonium chloride solution and with saturated sodium chloride solution, and the organic phase is separated off and concentrated in a rotary evaporator. Chromatography of the residue on silica gel with dichloromethane/methanol (100:1) afforded the product still in 57% purity and was employed without further purification in the next reaction.

Rf: 0.86 (dichloromethane/methanol 10:1)

EXAMPLES

The carbamates were prepared using sodium hydride in tetrahydrofuran (THF) or without other base in pyridine as solvent. The illustrated examples are given below for each of the two reaction routes.

1. 4-Amino-2-[1-(2-fluorobenzyl)-1H-pyrazolo[3,4-b]pyridin-3-yl]-5-pyrimidinyl 1-pyrrolidinecarboxylate

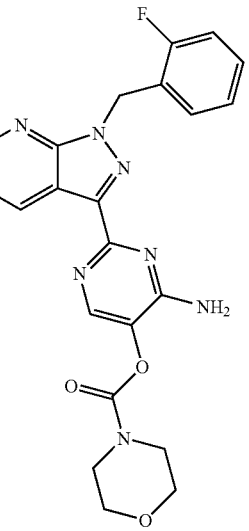

3.5 mg (0.15 mmol) of sodium hydride were added to a suspension of 50.0 mg (0.15 mmol) of 4-amino-2-[1-(2-fluorobenzyl)-1H-pyrazolo[3,4-b]pyridin-3-yl]-5-pyrimidinol from example IV in 2 ml of THF at RT. After the mixture had been stirred at RT for 30 min, 21.8 mg (0.16 mmol) of 1-pyrrolidinecarbonyl chloride were added and the mixture was stirred at RT overnight. The product was purified by thin-layer chromatography (silica gel, $CH_2Cl_2$/MeOH 10:1).

Yield: 50.4 g (78.2%) $^1$H-NMR: (400 MHz, DMSO-$d_6$): $\delta$=1.81-1.93 (m, 4H), 3.22 (t, J=6.5 Hz, 2H), 3.57 t, J=6.5 Hz, 2H), 5.81 (s, 2H), 7.05-7.30 (m, 5H), 7.31-7.44 (m, 2H), 8.12 (s, 1H), 8.63 (d, J=4.4 Hz, 1H), 8.92 (d, J=7.9 Hz, 1H). MS: ESI pos.), m/z=434.4 ([M+H]$^+$)

The following were obtained in the same way:

| Ex. | Formula | Yield (%) | 1H-NMR |
|---|---|---|---|
| 2 (from IV and 4-morpholinecarbonyl chloride) | | 85 | 1H-NMR: (300 MHz, DMSO-$d_6$): $\delta$=3.37-3.77(m, 8H), 5.82 (s, 2H), 7.05-7.30 (m, 5H), 7.31-7.44 (m, 2H), 8.12 (s, 1H), 8.64 (d, J=4.4 Hz, 1H), 8.94 (d, J=7.9Hz, 1H). |

3. 4-Amino-2-[1-(2-fluorobenzyl)-1H-pyrazolo[3,4-b]pyridin-3-yl]-5-pyrimidinyl diethylcarbamate

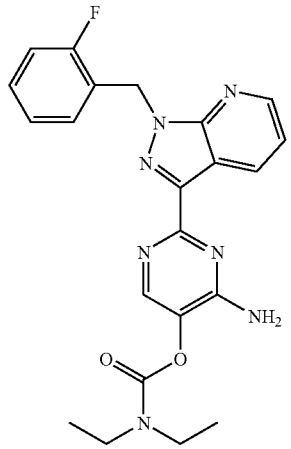

100 g (0.297 mmol) of 4-amino-2-[1-(2-fluorobenzyl)-1H-pyrazolo[3,4-b]pyridin-3-yl]-5-pyrimidinol from example IV are suspended in 15 ml of anhydrous pyridine and heated to 110° C. 48.4 mg (0.357 mmol) of N,N-diethylcarbamoyl chloride are added thereto, and the mixture is stirred at 110° C. for 2 h. The reaction solution is then concentrated in a rotary evaporator. The residue is chromatographed on silica gel with dichloromethane/methanol 100:1.

Yield: 90.5 g (69.9%) Rf: 0.86 (dichloromethane/methanol 10:1) $^1$H-NMR: (200 MHz, D$_6$DMSO), δ=1.07-1.28 (m, 6H, CH$_3$CH$_2$), 3.22-3.53 (m, 4H, CH$_3$CH$_2$), 5.83 (s, 2H, CH$_2$), 7.10-7.42 (m, 7H, Ar—H and NH$_2$), 8.09 (s, 1H, pyrimidine-H), 8.63 (dd, 1H, pyridine-H), 8.94 (dd, 1H, pyridine-H) MS: (ESI pos.), m/z=436.2 ([M+H]$^+$), 871.0 ([2M+H]$^+$)

The following was prepared analogously:

4. 1-{4-Amino-2-[1-(2-fluorobenzyl)-1H-pyrazolo[3,4-b]pyridin-3-yl]-5-pyrimidinyl}tert-butyl-1,4 piperazinedicarboxylate

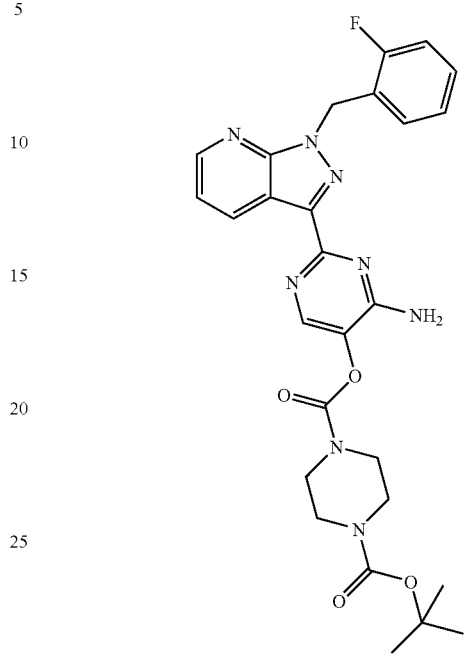

Yield: 36.4% Rf: 0.77 (dichloromethane/methanol 10:1) $^1$H-NMR: (200 MHz, D$_6$-DMSO). The spectrum exhibits E/Z rotamerism of the carbamate group. δ=1.39 and 1.42 (2s, 9H, C(CH$_3$)$_3$), 3.09-3.14 (m, 1H, piperazine-H), 3.26-3.34 (m, 1H, piperazine-H), 3.36-3,48 (br.s, 6H, piperazine-H), 3.52-3.64 (br.s, 2H, piperazine-H), 5.81 (s, 2H, CH$_2$), 7.10-7.27 (m, 5H, ArH and NH$_2$), 7.30-7.40 (m, 2H, Ar—H), 8.12 (s, 1H, pyrimidine-H), 8.63 (dd, 1H, pyridine-H), 8.94 (dd, 1H, pyridine-H) MS: (ESI pos.), m/z=549.1 ([M+H]$^+$)

The following were prepared analogously:

| Ex. | Formula | Yield (%) | Spectroscopic data |
|---|---|---|---|
| 5 (from IV and 4-piperazinecarbonyl chloride)) | | 68 | MS-ESI pos. (m/z): 491.1 [M + H]$^+$ Retention time (min): 3.87 (method B) Rf CH$_2$Cl$_2$/MeOH 10:1:0.39 |

-continued

| Ex. | Formula | Yield (%) | Spectroscopic data |
|---|---|---|---|
| 6 (from IV and N-isopropyl-N-methyl-aminocarbonyl chloride) | 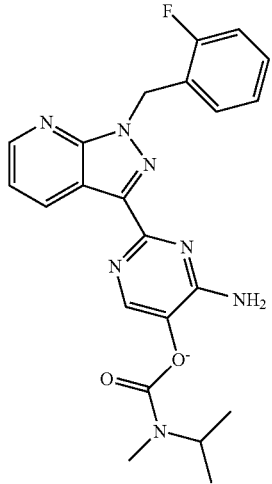 | 67 | MS-ESI pos. (m/z): 436.2 [M + H]$^+$, 870.92 [2 M + H]$^+$ Retention time (min). 4.19 (method B) Rf CH$_2$Cl$_2$/MeOH 10:1:0.91 |
| 7 (from IV and N-ethyl-N-methyl-aminocarbonyl chloride) | 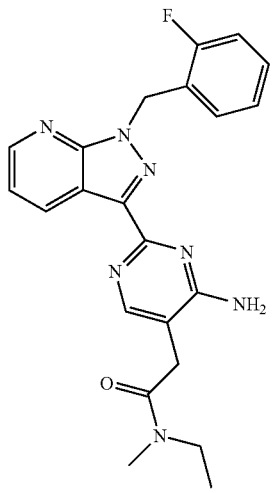 | 64 | MS-ESI pos. (m/z): 422.0 [M + H]$^+$, 842.9 [2 M + H]$^+$ Retention time (min): 4.07 (method B) Rf CH$_2$Cl$_2$/MeOH 10:1:0.90 |
| 8 (from IV and N-(1-cyano-1-methylethyl)-N-methyl-aminocarbonyl chloride) | 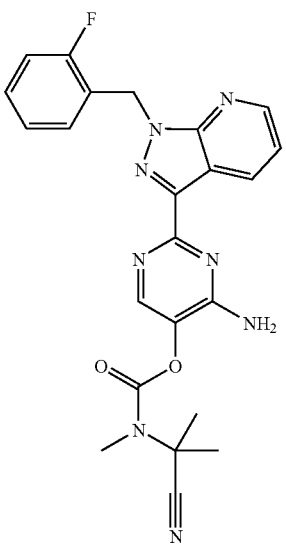 | 35 | MS-ESI pos. (m/z): 461.2 [M + H]$^+$ Retention time (min): 4.19 (method B) Rf CH$_2$C$_2$/MeOH 10:1:0.84 |

-continued

| Ex. | Formula | Yield (%) | Spectroscopic data |
|---|---|---|---|
| 9 (from IV and N,N-dimethyl-aminocarbonyl chloride) | | 63 | MS-ESI pos. (m/z): 408.3 [M + H]$^+$, 814.9 [2 M + H]$^+$ Retention time (min): 3.96 (method B) Rf CH$_2$Cl$_2$/MeOH 10:1:0.73 |
| 10 (from IV and N,N-diisopropyl-aminocarbonyl chloride) | | 58 | MS-ESI pos. (m/z): 464 [M + H]$^+$, 927 [2 M + H]$^+$ Retention time (min): 4.44 (method B) Rf CH$_2$Cl$_2$/MeOH 10:1: |
| 11 (from IV and N,N-diallyl-aminocarbonyl chloride) | | 45 | MS-ESI pos. (m/z): 460 [M + H]$^+$ Retention time (min): 4.34 (method B) Rf CH$_2$Cl$_2$/MeOH 10:1: |

| Ex. | Formula | Yield (%) | Spectroscopic data |
|---|---|---|---|
| 12 (from IV and N-2-chloroethyl-N-methyl-aminocarbonyl chloride) | | 39 | MS-ESI pos. (m/z): 456 [M + H]+ Retention time (min): 4.16 (method B) Rf CH$_2$Cl$_2$/MeOH 10:1: |
| 13 (from IV and 2-ethoxycarbonyl-piperidine-N-carbonyl chloride) | | 21 | MS-ESI pos. (m/z): 520 [M + H]+, 1039 [2 M + H]+ Retention time (min): 4.39 (method B) Rf CH$_2$Cl$_2$/MeOH 10:1: |
| 14 (from IV and N,N-diethylthiocarbonyl chloride) | | 79.1 | MS-ESI pos. (m/z): 452 [M + H]+ Retention time (min): 4.43 (method B) |

| Ex. | Formula | Yield (%) | Spectroscopic data |
|---|---|---|---|
| 15 (from IV and N-(2-methoxy-1-methylethyl-(ethoxycarbonyl-methyl-aminocarbonyl chloride)) | | 62 | MS-ESI pos. (m/z): 538.2 [M + H]+ Retention time (min): 4.39 (method B) |
| 16 (from IV and N-methyl-N-cyclohexylamino-carbonyl chloride) | | 67.6 | MS-ESI pos. (m/z): 538.2 [M + H]+ Retention time (min): 4.53 (method B) |
| 17 (from IV and N-ethyl-N-phenylamino-carbonyl chloride) | | 71.4 | MS-ESI pos. (m/z): 484 [M + H]+ Retention time (min): 4.47 (method B) |

| Ex. | Formula | Yield (%) | Spectroscopic data |
|---|---|---|---|
| 18 (from IV and N-methyl-N-methoxyethyl-aminocarbonyl chloride) | 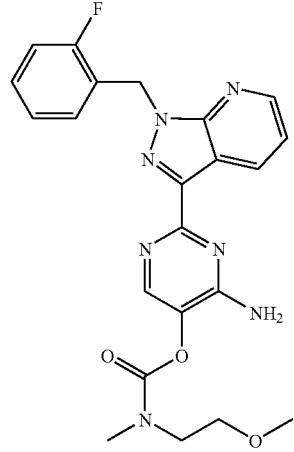 | 28.5 | MS-ESI pos. (m/z): 452.3 [M + H]$^+$ Retention time (min): 4.10 (method B) |
| 19 (from IV and N,N-dimethylthio-carbonyl chloride) | 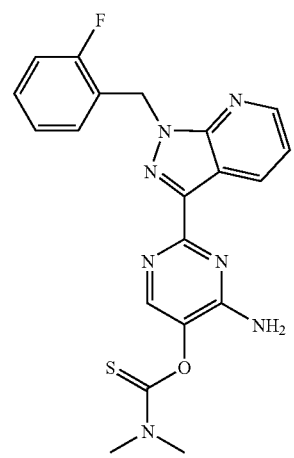 | 70.4 | MS-ESI pos. (m/z): 424 [M + H]$^+$ Retention time (min): 4.20 (method B) |
| 20 (from IV and N-2-butyl-N-ethoxycarbonyl-methylamino-carbonyl chloride) | 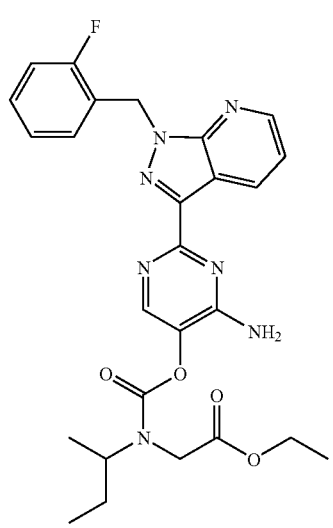 | 57.7 | MS-ESI pos. (m/z): 522 [M + H]$^+$, 1043 [2 M + H]$^+$ Retention time (min): 4.47 (method B) |

-continued

| Ex. | Formula | Yield (%) | Spectroscopic data |
|---|---|---|---|
| 21 (from IV and N-methyl-N-(1,3-dioxolan-2-yl)-methylamino-carbonyl chloride) | | 22.2 | MS-ESI pos. (m/z): 480 [M + H]$^+$ Retention time (min): 4.05 (method B) |
| 22 (from IV and N-(p-tolyl)-N-(2-cyanoethyl)-aminocarbonyl chloride) | | 20.4 | MS-ESI pos. (m/z): 523 [M + H]$^+$ Retention time (min): 4.37 (method B) |
| 23 (from IV and 1,2,3,4-tetrahydro-quinoline-N-carbonyl chloride) | | 15.4 | MS-ESI pos. (m/z): 496 [M + H]$^+$ Retention time (min): 4.45 (method B) |

24. 4-Amino-2-[1-(2-fluorobenzyl)-1H-pyrazolo[3,4-b]pyridin-3-yl]-5-pyrimidinyl 2-methoxyethylcarbamate

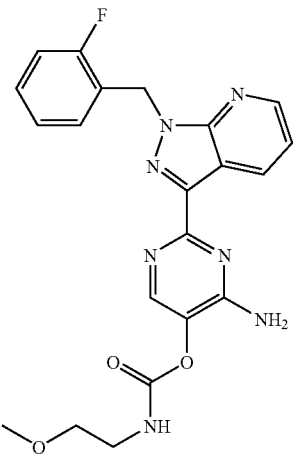

160.3 mg (0.29 mmol) of 4-amino-2-[1-(2-fluorobenzyl)-1H-pyrazolo[3,4-b]pyridin-3-yl]-5-pyrimidinyl 4-methoxybenzyl(2-methoxyethyl)carbamate from example IX are dissolved in 3 ml of trifluoroacetic acid and stirred at 60° C. for 6 h. For workup, 10 the reaction solution is poured into ice-water, cautiously neutralized with sodium bicarbonate and extracted 3× with dichloromethane, and the org. phase is dried over sodium sulfate and concentrated. The residue is chromatographed on silica gel with dichloromethane/methanol (30:1).

Yield: 28.3 g (22.5%) Rf: 0.88 (dichloromethane/methanol 10:1) $^1$H-NMR: (200 MHz, CDCl$_3$): δ=3.39 (s, 3H, OCH3), 3.43-3.58 (m, 4H, CH2-CH2), 5.15-5.28 (br. s, 2H, NH2), 5.50-5.63 (m, 1H, NH), 5.93 (s, 2H, CH2), 6.86-7.30 (m, 5H, Ar—H), 8.37 (s, 1H, Ar—H), 8.59 (dd, 1H, Ar—H), 8.92 (dd, 1H, Ar—H). MS: ESI pos.: m/z=438.2 [M+H]$^+$

25. 4-Amino-2-[1-(2-fluorobenzyl)-1H-pyrazolo[3,4-b]pyridin-3-yl]-5-pyrimidinyl 1-piperazinecarboxylate

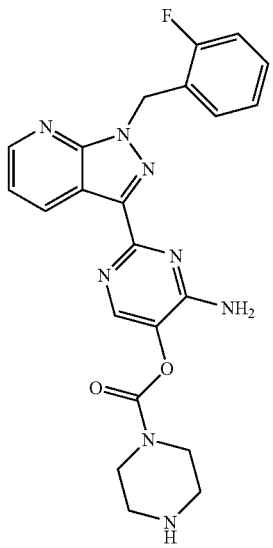

214.2 mg (0.390 mmol) of 1-{4-amino-2-[1-(2-fluorobenzyl)-1H-pyrazolo[3,4-b]pyridin-3-yl]-5-pyrimidinyl}4-tert-butyl 1,4-piperazinedicarboxylate from example 4 are dissolved in 5 ml of dichloromethane, and 5 ml of trifluoroacetic acid are added. The mixture is left to stir at room temperature for 1 h. For workup, it is neutralized with 1 N sodium hydroxide solution and extracted three times with dichloromethane. The organic phase is dried over sodium sulfate and concentrated in a rotary evaporator.

Yield: 123.1 mg (64.0%) Rf: 0.16 (dichloromethane/methanol 10:1) $^1$H-NMR: (200 MHz, D$_6$-DMSO): δ=2.67-2.81 (br.s, 4H, piperazine H), 3.21-3.41 (br.s, 2H, piperazine H, coincident with H$_2$O signal), 3.42-3.59 (br.s, 2H, piperazine H), 5.81 (s, 2H, CH$_2$), 7.08-7.41 (m, 7H, Ar—H and NH$_2$), 8.10 (s, 1H, pyrimidine H), 8.63 (dd, 1H, pyridine H), 8.92 (dd, 1H, pyridine H) MS: (ESI pos.), m/z=449.2 ([M+H]$^+$)

26. 4-{[(Diethylamino)carbonyl]amino}-2-[1-(2-fluorobenzyl)-1H-pyrazolo[3,4-b]pyridin-3-yl]-5-pyrimidinyl diethylcarbamate

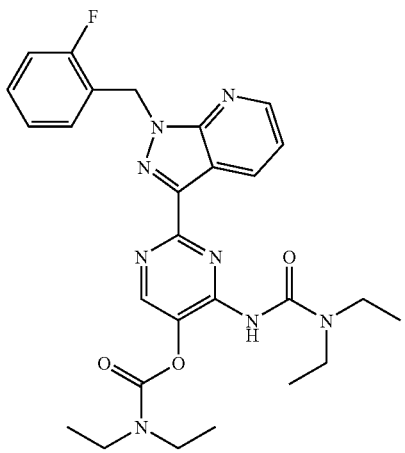

100 mg (0.297 mmol) of 4-amino-2-[1-(2-fluorobenzyl)-1H-pyrazolo[3,4-b]pyridin-3-yl]-5-pyrimidinol from example IV are suspended in 5 ml of anhydrous THF, and 7.51 mg (0.297 mmol) of sodium hydride (95%) are added. The mixture is left to stir at room temperature for 30 min. Then 44.35 mg (0.327 mmol) of N,N-diethylcarbamoyl chloride are added, and the mixture is left to stir at room temperature overnight. Water is cautiously added, and the mixture is extracted three times with ethyl acetate. The organic phase is dried over sodium sulfate and concentrated in a rotary evaporator. The residue is chromatographed on silica gel with dichloromethane/methanol 100:1 and then by preparative HPLC (column: Kromasil 100 C 18 5 μm 250×20 mm No. 101132R, flowrate: 25 ml/min, temp. 50° C., water-acetonitrile 50/50).

Yield: 29.9 g (18.8%) Rf: 0.88 (dichloromethane/methanol 10:1) $^1$H-NMR: (400 MHz, D$_6$-DMSO): δ=1.07-1.19 (m, 12H, CH$_3$CH$_2$), 3.26-3.41 (m, 8H, CH$_3$CH$_2$), 5.85 (s, 2H, CH$_2$), 7.11-7.44 (m, 5H, Ar—H), 8.52 (s, 1H, pyrimidine H), 8.68 (dd, 1H, pyridine H), 9.02 (dd, 1H, pyridine H), 9.39 (br,s, 1H, NH)

27. 4-Amino-2-[1-(2-fluorobenzyl)-1H-pyrazolo[3,4-b]pyridin-3-yl]-5-pyrimidinyl methylcarbamate

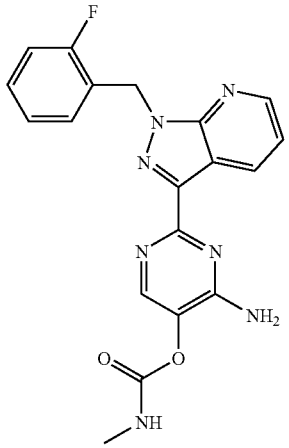

562.5 mg (1.04 mmol) of 4-amino-2-[1-(2-fluorobenzyl)-1H-pyrazolo[3,4-b]pyridin-3-yl]-5-pyrimidinyl 3,4-dimethoxybenzyl(methyl)carbamate from example VI are dissolved in 10 ml of trifluoroacetic acid and stirred at 60° C. for 4 h. For workup, the reaction solution is poured into ice-water, cautiously neutralized with sodium bicarbonate and extracted three times with dichloromethane, and the organic phase is dried over sodium sulfate and concentrated. The residue is chromatographed on silica gel with dichloromethane/methanol (initially 100:1, then 30:1).

Yield: 123.8 g (30.4% over 2 stages) MS(MALDI pos.): m/z=394.18 ([M+H]$^+$), 416.15 ([M+Na]$^+$) Rf: 0.67 (dichloromethane/methanol 10:1) $^1$H-NMR: (200 MHz, D$_6$-DMSO). The spectrum exhibits E/Z rotamerism of the carbamate group. The following describes only the signals of the main rotamer: δ=2.70 (d, 3H, CH$_3$), 5.81 (s, 2H, CH$_2$), 7.07-7.41 (m, 7H, Ar—H and NH$_2$), 7.62 (br. q, 1H, NH), 8.11 (s, 1H, pyrimidine H), 8.62 (dd, 1H, pyridine H), 8.93 (dd, 1H, pyridine H)

28. 4-Amino-2-[1-(2-fluorobenzyl)-1H-pyrazolo[3,4-b]pyridin-3-yl]-5-pyrimidinyl allyl(cyclopentyl) carbamate

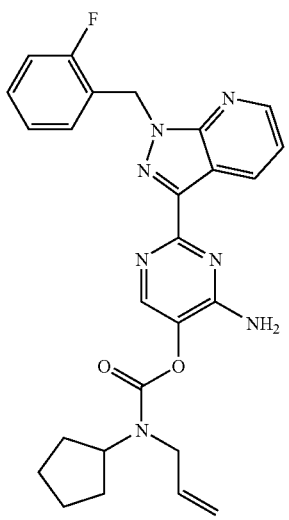

100 mg (0.297 mmol) of 4-amino-2-[1-(2-fluorobenzyl)-1H-pyrazolo[3,4-b]pyridin-3-yl]-5-pyrimidinol from example IV are suspended in 15 ml of anhydrous pyridine and heated to 110° C. 67.0 mg (0.357 mmol) of allyl (cyclopentyl)carbamoyl chloride from example VII are added to this in portions, and the mixture is left to stir at 110° C. for 2 h. For workup, the reaction solution is concentrated, the residue is taken up in dichloromethane and extracted once with saturated ammonium chloride solution and once with saturated NaCl solution, and the organic phase is dried over Na$_2$SO$_4$ and concentrated in a rotary evaporator. The residue is chromatographed on silica gel with dichloromethane/methanol 100:1.

Yield: 105 mg (72%) Rf: 0.92 (dichloromethane/methanol 10:1) $^1$H-NMR: (200 MHz, D$_6$-DMSO), δ=1.37-1.98 (br. m, 8H, cyclopentyl-CH$_2$), 3.80-4.05 (br. m, 2H, allyl-CH$_2$N), 4.22-4.53 (br. m, 1H, cyclopentyl CHN), 5.07-5.29 (br. m, 2H, 2H, olefinic allyl CH$_2$), 5.80-6.10 (br. m, 1H, olefinic allyl CH), overlapped by 5.81 (s, 2H, CH$_2$), 7.04-7.41 (m, 7H, Ar—H and NH$_2$), 8.08 (s, 1H, pyrimidine H), 8.64 (dd, 1H, pyridine H), 8.92 (dd, 2H, pyridine H) MS: (ESI pos.), m/z=488 ([M+H]$^+$), 975 ([2M+H]$^+$)

29. N-[({4-Amino-2-[1-(2-fluorobenzyl)-1H-pyrazolo[3,4-b]pyridin-3-yl]-5-pyrimidinyl}oxy)carbonyl]-N-(sec-butyl)glycine

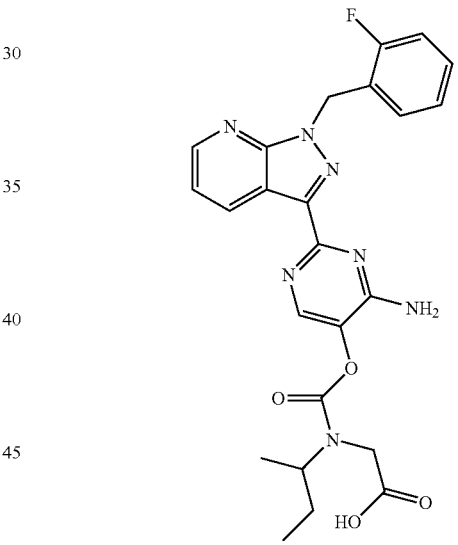

73.5 mg (0.141 mmol) of ethyl N-[({4-amino-2-[1-(2-fluorobenzyl)-1H-pyrazolo[3,4-b]pyridin-3-yl]-5-pyrimidinyl}oxy)carbonyl]-N-(sec-butyl)glycinate from example 20 are dissolved in 3 ml of THF/water/methanol 1:1:1. 5.1 mg (0.12 mmol) of lithium hydroxide monohydrate are added to this, and the mixture is left to stir at RT for 1 h. Workup involves extraction 3× with 10 ml of CH$_2$Cl$_2$ each time and 1× with saturated NaCl solution, drying over Na$_2$SO$_4$ and concentration to dryness in a rotary evaporator.

The residue is purified by preparative HPLC (column: Cromsil 120 ODS, C-18, 10 μm, 250×30 mm, flowrate 50 nl/min, room temp., gradient: water acetonitrile at 0 min: 90:10, at 28 min 5:95).

Rf: 0.25 (CH$_2$Cl$_2$/CH$_3$OH 10:1) HPLC retention time: 3.55 (method F) MS-ESI pos.: (m/z): 494.3 μM+H]$^+$, 987.3 [2 M+H]$^+$.

The invention claimed is:

1. A method for the treatment of sexual dysfunction, comprising administering to a patient an effective amount of a compound of the formula (I)

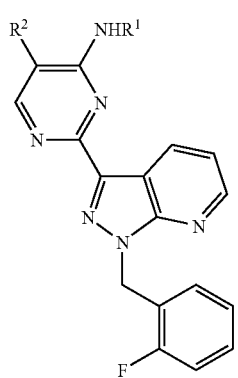

(I)

in which
R$^1$ is hydrogen or a di-C$_{1-6}$-alkylaminocarbonyl radical,
R$^2$ is a radical of the formula —O—CX—NR$^3$R$^4$, where
X is O or S;
R$^3$ and R$^4$ may be identical or different from one another and each is a radical chosen from H, optionally substituted C$_{1-6}$-alkyl, optionally substituted C$_{1-6}$-alkoxy-C$_{1-6}$-alkyl, optionally substituted hydroxy-C$_{1-6}$-alkyl, optionally substituted C$_{2-6}$-alkenyl, optionally substituted C$_{1-6}$-alkylcarbonyloxy-C$_{1-6}$-alkyl, optionally substituted C$_{1-6}$-alkoxycarbonyl-C$_{1-6}$-alkyl, optionally substituted hydroxycarbonyl-C$_{1-6}$-alkyl, phenyl which is optionally substituted by a C$_{1-6}$-alkyl radical, a saturated five- to seven-membered heterocycle which is optionally linked via a C$_{1-6}$-alkyl radical to the nitrogen atom, and optionally substituted C$_{3-8}$-cycloalkyl, where R$^3$ and R$^4$ cannot simultaneously be H;
or
R$^3$ and R$^4$ together with the nitrogen atom to which they are bonded form a five- to seven-membered saturated heterocycle which may optionally contain a further heteroatom chosen from N, O, and S and/or may optionally be substituted or fused to a phenyl ring;
or a salt, stereoisomer, tautomer, or hydrate thereof.

2. The method according to claim 1, wherein the compound of the formula (I) is employed in combination with at least one organic nitrate or NO donor or in combination with at least one compound which inhibits the breakdown of cyclic guanosine monophosphate (cGMP).

3. A process for producing medicaments, which comprises converting at least one compound of the formula (I)

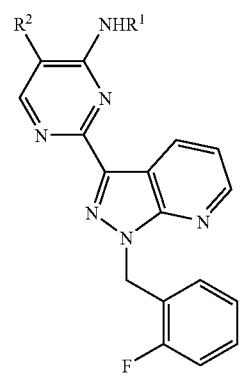

(I)

in which
R$^1$ is hydrogen or a di-C$_{1-64}$-alkylaminocarbonyl radical,
R$^2$ is a radical of formula —O—CX—NR$^3$R$^4$, where
X is O or S;
R$^3$ and R$^4$ may be identical or different from one another and each is a radical chosen from H, optionally substituted C$_{1-6}$-alkyl, optionally substituted C$_{1-6}$-alkoxy-C$_{1-6}$-alkyl, optionally substituted hydroxy-C$_{1-6}$-alkyl, optionally substituted C$_{2-6}$-alkenyl, optionally substituted C$_{1-6}$-alkylcarbonyloxy-C$_{1-6}$-alkyl, optionally substituted C$_{1-6}$-alkoxycarbonyl-C$_{1-6}$-alkyl, optionally substituted hydroxycarbonyl-C$_{1-6}$-alkyl, phenyl which is optionally substituted by a C$_{1-6}$-alkyl radical, a saturated five- to seven-membered heterocycle which is optionally linked via a C$_{1-6}$-alkyl radical to the nitrogen atom, and optionally substituted C$_{3-8}$-cycloalkyl, where R$^3$ and R$^4$ cannot simultaneously be H; or
R$^3$ and R$^4$ together with the nitrogen atom to which they are bonded form a five- to seven-membered saturated heterocycle which may optionally contain a further heteroatom chosen from N, O, and S and/or may optionally be substituted or fused to a phenyl ring;
or a salt, stereoisomer, tautomer, or hydrate thereof, where appropriate with conventional excipients and additives, into a suitable administration form.

* * * * *